(12) United States Patent
Dworak et al.

(10) Patent No.: US 10,351,305 B2
(45) Date of Patent: Jul. 16, 2019

(54) PACKAGE SEAL HAVING A FIBROUS BREATHABLE MATERIAL

(71) Applicant: AMCOR FLEXIBLES, INC., Mundelein, IL (US)

(72) Inventors: Adam Jan Dworak, Northbrook, IL (US); Brian Ingraham, Madison, WI (US)

(73) Assignee: AMCOR FLEXIBLES, INC., Mundelein, IL (US)

( * ) Notice: Subject to any disclaimer, the term of this patent is extended or adjusted under 35 U.S.C. 154(b) by 324 days.

(21) Appl. No.: 15/358,672

(22) Filed: Nov. 22, 2016

(65) Prior Publication Data

US 2017/0144802 A1 May 25, 2017

Related U.S. Application Data

(60) Provisional application No. 62/258,907, filed on Nov. 23, 2015.

(51) Int. Cl.
| | |
|---|---|
| *B65B 5/02* | (2006.01) |
| *B65B 5/04* | (2006.01) |
| *B65B 7/02* | (2006.01) |
| *B65B 9/04* | (2006.01) |
| *A61B 50/00* | (2016.01) |
| *A61B 50/30* | (2016.01) |

(Continued)

(52) U.S. Cl.
CPC .............. *B65D 33/01* (2013.01); *A61B 50/30* (2016.02); *A61B 50/33* (2016.02); *A61F 13/0008* (2013.01); *A61F 13/00072* (2013.01); *A61F 15/001* (2013.01); *B65B 5/022* (2013.01); *B65B 5/045* (2013.01); *B65B 7/02* (2013.01); *B65B 9/045* (2013.01); *B65B 55/18* (2013.01); *B65B 61/182* (2013.01); *B65D 33/18* (2013.01); *B65D 75/30* (2013.01); *B65D 75/5894* (2013.01); *A61B 2050/0065* (2016.02); *A61B 2050/3014* (2016.02); *A61B 2050/314* (2016.02)

(58) Field of Classification Search
CPC .................................................... B65D 33/01
USPC ........................................................ 53/425
See application file for complete search history.

(56) References Cited

U.S. PATENT DOCUMENTS

| | | |
|---|---|---|
| 3,685,720 A | 8/1972 | Brady |
| 3,761,013 A | 9/1973 | Schuster |

(Continued)

FOREIGN PATENT DOCUMENTS

| | | |
|---|---|---|
| EP | 0 846 445 | 6/1998 |
| JP | H 06050611 | 7/1994 |

(Continued)

OTHER PUBLICATIONS

Office Action for corresponding European Application No. 13724924.9 dated Mar. 9, 2017.

(Continued)

*Primary Examiner* — Lori L Baker
(74) *Attorney, Agent, or Firm* — Alston & Bird LLP

(57) ABSTRACT

The invention provides a sterilizable pouch having at least one wall formed of a flexible film and including an opening formed therein for providing communication to an interior space of the package. A breathable material is disposed on an outer surface of the wall covering the opening. The breathable material is joined to the outer surface of the wall with a continuous heat seal. A heat resistant material is positioned between the breathable material an outer surface of the wall.

27 Claims, 6 Drawing Sheets

(51) Int. Cl.
  *A61B 50/33* (2016.01)
  *A61F 13/00* (2006.01)
  *A61F 15/00* (2006.01)
  *B65B 55/18* (2006.01)
  *B65B 61/18* (2006.01)
  *B65D 33/01* (2006.01)
  *B65D 33/18* (2006.01)
  *B65D 75/30* (2006.01)
  *B65D 75/58* (2006.01)

(56) References Cited

U.S. PATENT DOCUMENTS

| | | |
|---|---|---|
| 4,881,649 A | 11/1989 | Hsu et al. |
| 5,551,781 A | 9/1996 | Wilkes et al. |
| 5,590,778 A | 1/1997 | Dutchik |
| 5,773,136 A | 6/1998 | Alder et al. |
| 5,965,254 A | 10/1999 | Christopherson et al. |
| 5,976,299 A | 11/1999 | Ivey |
| 5,997,968 A | 12/1999 | Dries et al. |
| 6,080,456 A | 6/2000 | Fonteyne |
| 6,117,505 A | 9/2000 | Weiss et al. |
| 6,189,694 B1 | 2/2001 | Weiss et al. |
| 6,231,975 B1 | 5/2001 | Kong et al. |
| 6,234,310 B1 | 5/2001 | Goldhaber |
| 6,251,489 B1 | 6/2001 | Weiss et al. |
| 6,279,745 B1 | 8/2001 | Huynen et al. |
| 6,451,426 B2 | 9/2002 | Kong et al. |
| 6,632,313 B2 | 10/2003 | Nickel et al. |
| 6,770,361 B2 | 8/2004 | Kong |
| 6,828,019 B2 | 12/2004 | Kong et al. |
| 6,893,672 B2 | 5/2005 | Ingraham |
| 6,896,956 B2 | 5/2005 | Kong |
| 6,960,392 B2 | 11/2005 | Le Du et al. |
| 7,354,635 B2 | 4/2008 | Malfait et al. |
| 7,434,372 B2 | 10/2008 | Vanhamel et al. |
| 7,758,484 B2 | 7/2010 | Peterson |
| 8,048,501 B2 | 11/2011 | Singh |
| 8,062,723 B2 | 11/2011 | Singh |
| 8,070,188 B2 | 12/2011 | Cronley |
| 8,071,188 B2 | 12/2011 | Singh |
| 2004/0115457 A1 | 6/2004 | Kong |
| 2004/0166259 A1 | 8/2004 | Merritt |
| 2005/0255980 A1 | 11/2005 | Ventura et al. |
| 2011/0127188 A1 | 6/2011 | Thompson et al. |
| 2011/0229372 A2 | 9/2011 | Whitehead et al. |
| 2012/0247072 A1 | 10/2012 | Romijn et al. |
| 2014/0133785 A1 | 5/2014 | Diviesti et al. |

FOREIGN PATENT DOCUMENTS

| | | |
|---|---|---|
| JP | 2001-524038 | 11/2001 |
| JP | 2003-211565 | 7/2003 |
| JP | 2007 276803 A | 10/2007 |
| JP | 2010 268967 A | 12/2010 |
| WO | WO-96/04178 | 2/1996 |
| WO | WO-98/45115 | 10/1998 |
| WO | WO-2011/038961 | 4/2011 |

OTHER PUBLICATIONS

Office Action for corresponding Japanese Application No. 2015-543030 dated Jan. 27, 2017.
International Search Report and Written Opinion for Application No. PCT/IB2016/057078, dated Feb. 22, 2017.
Decision to Grant Patent for Japanese Application No. 2015-543030 dated Aug. 18, 2017.
Second Written Opinion of the International Preliminary Examining Authority from International Application No. PCT/IB2016/057078, dated Oct. 20, 2017, 6 pages.
International Preliminary Report on Patentability (Chapter II) from International Application No. PCT/IB2016/057078, dated Dec. 6, 2017, 12 pages.
Office Action for corresponding European Application No. 13724924.9 dated Mar. 5, 2018, 6 pages.
Communication under Rule 71(3) for corresponding European Application No. 13724924.9 dated May 22, 2018, 69 pages.
International Preliminary Report on Patentability for Application No. PCT/US2013/036687 dated Feb. 19, 2015.
International Search Report and Written Opinion for Application No. PCT/US2013/036687, dated Jul. 3, 2013.
Office Action for corresponding U.S. Appl. No. 13/677,475 dated Apr. 7, 2016.
Office Action for corresponding U.S. Appl. No. 13/677,475 dated Jul. 31, 2014.
Office Action for corresponding U.S. Appl. No. 13/677,475 dated May 22, 2015.
Office Action for corresponding U.S. Appl. No. 13/677,475 dated Nov. 14, 2016.
Office Action for U.S. Appl. No. 13/677,475 dated Jun. 16, 2017.

PACKAGE SEAL HAVING A FIBROUS BREATHABLE MATERIAL

CROSS REFERENCE TO RELATED APPLICATION

This application claims priority to U.S. Provisional Application No. 62/258,907, filed Nov. 23, 2015, the entirety of which are incorporated herein by reference.

FIELD

The present invention is directed to a package for sterilizing articles, and more particularly, a package for the packaging and sterilization of medical devices.

BACKGROUND

Containers in which a fibrous sheet material is sealed to itself or a polymeric film sheet have been used in a variety of different applications. One such application is directed to a container for packaging articles that are to be sterilized.

Sterilizable containers in the form of pouches or bags, sealed trays, and envelopes are popular vehicles for storing and transporting sterile articles, including instruments, dressings, drapes, etc. Typically, such containers include sheet of a fibrous breathable material that is both a microbe barrier and is gas pervious. After the article has been sealed in the container, the container is treated with a sterilizing gas that is introduced into the interior of the container through the fibrous breathable material. The porous characteristics of the fibrous breathable material allows a sterilizing medium, such as sterilizing gas (e.g., steam, ethylene oxide, etc.) to pass into and out of the container, while forming a sterile barrier against bacteria or other contaminants.

One such container comprises a pouch or bag comprising a polymeric sheet and a sheet of a fibrous breathable material, such as paper or TYVEK®, that are positioned face-to-face and sealed to each other along their common peripheral edges to form seams defining a pouch. The pouch or bag is typically opened by cutting or peeling off of the fibrous breathable material.

Another example of a sterilizable container comprises a container in which two sheets of polymeric film are sealed to each other along peripheral edges to form seams defining a pouch. The pouch includes an access opening formed in one of the film sheets through which a sterilizing gas can be introduced into the interior space of the pouch. In this type of container, the access opening is covered by the fibrous breathable material, also referred to as a "header," that is sealed to the outer surface of the pouch. These types of containers may be opened via a tear notch located at one end of the pouch that can be used to linearly tear the film and gain access to the contents of the pouch.

Alternatively, the fibrous breathable material can be removed by peeling it away from the film sheet to thereby gain access to the sterilized article through the access opening. In order for the header to be easily removed to gain access to the opening, the fibrous breathable material is typically coated so that the material is peelable from the surface of the package. Unfortunately, the presence of a coating results in a substantial decrease in the porosity, and hence breathability of the breathable material. This in turn results in longer sterilization times to ensure that an effective amount of sterilization gas is introduced into the package. In order to address this problem, packages have been developed in which the size of the opening is greatly increased to thereby improve the overall breathability of the package. However, such designs necessarily require an increased amount of breathable material in order to cover the opening, which results in higher production costs.

Another common package for packaging of medical devices is a blister-type package in which a sheet of the fibrous breathable material is sealed to the peripheral edge of a tray to form a lidding. After an article has been sealed in one of these types of packages, a sterilizing gas can then be introduced into the interior of the package through the breathable membrane. These types of packages are typically opened by either cutting or tearing off of the fibrous breathable material in order to gain access to the article packaged therein.

All of the aforementioned containers present disadvantages. First, in the packaging of sterilized articles, it is important to maintain a sterile and aseptic presentation upon opening of the container. Tyvek®, which is widely used as a microbe barrier material, is a nonwoven sheet material made of individual fibers that are thermally bonded to each other to form a coherent fabric. Opening of a container that includes a fibrous breathable material along a seam or by cutting may result in the creation of small fibers that may be deposited on the sterilized article. In addition, a problem that has been associated with the use of a coated breathable material is the release of particulate matter from the coating itself, or from the breathable material as it is removed from the container.

The release of such particulate matter and fibers can compromise the sterile field, and is therefore unacceptable.

Accordingly, there is a need for improved containers for packaging and sterilizing of articles, and in particular, for packaging and sterilizing of articles, devices and instruments to be used in medical applications.

SUMMARY

Embodiments of the present invention are directed to sterilizable containers that overcome many of the problems with the prior art.

In particular, the inventors of the present disclosure have now discovered that sterilizable packages in which an uncoated breathable material is directly adhered to an exterior surface of the sterilizable package may help overcome many of the problems of prior sterilizable packages. In particular, embodiments of the present invention are directed to sterilizable packages comprising front and back sheets of a flexible film are joined to each other along adjacent side edges to form side seams, and along one of the top or bottom edges to define a pouch having an interior space for receiving an article therein. At least one of the front or back sheets includes an opening formed therein for providing communication between an exterior environment of the pouch and the interior space of the pouch. A breathable material is disposed on an outer surface of the wall covering the opening, and is joined to the outer surface of the wall with a heat seal.

A side seam extends over the edges of the breathable material to thereby seal the breathable material to the front or back sheet. A heat resistant material is disposed between the breathable material and the film to selectively prevent adherence of the breathable material to the film.

In one embodiment, the invention provides a sterilizable pouch comprising first and second sheets (e.g., front and back sheets) of a flexible film joined to each other along opposing side and bottom edges to define a pouch having an interior space for receiving an article therein. An opening formed in at least one of the front or back sheets provides communication between an exterior environment of the pouch and the interior space. A breathable material overlies and covers the opening, and is joined to an outer surface of the front or back sheet with a continuous heat seal. Preferably, the breathable material comprising a fibrous material that is impervious to microorganisms, but pervious to gases, such as a paper or nonwoven sheet material. In one embodiment, the breathable material is uncoated. A heat resistant material is selectively disposed between the breathable material and the outer surface of the front or back sheet to prevent the breathable material from sealing to the outer surface of the front or back sheet.

In some embodiments, the heat resistant material comprises a polymer material having a melting temperature higher than that of the film to which the breathable material is attached. For example, the heat resistant material may comprise a strip of adhesive tape attached to an inner surface of the breathable material. In some embodiments, the heat resistant material is disposed between the breathable material and at least a portion of the side edges of the pouch.

In one embodiment, the continuous heat seal joining the breathable material includes a lower portion that is disposed below the opening of pouch such that the lower portion is disposed towards the bottom edge of the pouch, and wherein the heat resistant material is disposed between the lower portion and a peripheral edge of the breathable material. In particular, the breathable material may include a lip that is unconnected to the film and that extends between the continuous seam and a peripheral edge of the breathable material. In some embodiments, the lip extends between the continuous seam and a peripheral edge from about 0.5 to about 15 cm, and the heat resistant material is attached to an inner surface of the breathable material along the lip.

In one embodiment, the heat resistant material extends between opposing side edges of the pouch. In some embodiments, the opposing side edges of the front and back sheets are joined to each other with a heat seal defining side seams of the pouch, and the continuous heat seal joining the breathable material to the outer surface of said front sheet at least partially overlies said side seams, such that the heat resistant material is disposed between the breathable material and a portion of the side seams so that the heat resistant material prevents the breathable material from being sealed to the outer surface of the front or back sheets.

In one embodiment, the front and back sheets each include opposing top edges that are unconnected to each other to define an access opening into the interior space of the pouch.

In a further aspect, embodiments of the present invention may provide sterilizable pouch having front and back sheets of a flexible film arranged in opposing face-to-face relation, each having an inner surface comprising a heat sealable thermoplastic material on opposite surfaces, a top edge, a bottom edge, and opposite side edges extending longitudinally from said top edge to said bottom edge; In this embodiment, the pouch may include side seams extending longitudinally along said opposite side edges and joining the front and back sheets to each other, a bottom seam extending transversely along the bottom edges and joining the front and back sheets to each other, and an opening formed in the front sheet and providing communication between an exterior environment of the pouch and an interior space of the pouch.

As discussed previously, a breathable material is disposed on the front sheet covering the opening of the pouch. The breathable material comprises a moisture vapor permeable, water-impermeable sheet material, such as a nonwoven or paper sheet material. The breathable material is joined to the front sheet with a continuous seam located at or adjacent the peripheral edge of the breathable material.

A heat resistant material is disposed on an inner surface of the breathable material between the front sheet and the breathable material, such that the presence of the heat resistant material defines a region in which the breathable material is not joined to the front sheet.

In one embodiment, the breathable material comprises an uncoated nonwoven fabric.

Preferably, the top edges of the front and back sheet are unconnected to each other to define an access opening into the interior space of the pouch. Following introduction of an article into the interior space, the opposing top edges of the front sheet may be sealed to each other to enclose the article in the pouch.

In one embodiment, the heat resistant material extends between opposing side edges of the pouch. Alternatively, the heat resistant material does not extend between opposing side edges of the pouch, and is positioned in discrete locations between the side seams and the breathable material.

In a preferred embodiment, the heat resistant material comprises an adhesive strip having a film layer and an adhesive layer, wherein the adhesive layer joins the film layer to an inner surface of the breathable material. In one embodiment, the heat resistant material has a melting temperature that is at least 10° C. higher than the melting temperature of a polymer forming a heat sealable surface of the front and back sheets. In some embodiments, the melting point of the heat resistant material is 20° C. to 35° C. higher than a sealing temperature for sealing the breathable material to an outer surface of the front sheet.

In one aspect, the invention also provides a method of making a sterilizable pouch comprising the steps of forming an opening in a first sheet material of a flexible film; providing a breathable material having a heat resistant material joined to a surface of the breathable material; affixing the breathable material to an outer surface of the first sheet material with a continuous heat seal such that the breathable material overlies and covers said opening, wherein the heat resistant material is disposed between the outer surface of the first sheet and the breathable material; and joining a second sheet material of a flexible film to an opposite surface of the first sheet material via a plurality of side seams and a bottom seam to form a pouch having an interior space, wherein the heat resistant material prevents the inner surface of the breathable material from sealing to the outer surface of the front sheet.

In one embodiment, the first and second sheets each include opposing top edges that are unconnected to each other to define an access opening into an interior space of the pouch.

In some embodiments, the breathable material is affixed to the first sheet prior to joining the first and second sheets to each other. Alternatively, the breathable material may be affixed to the first sheet after joining the first and second sheets to each other.

In one embodiment, the opposite side edges of the first and second sheets are joined to each other with a heat seal defining side seams of the pouch, and wherein the continuous heat seal joining the breathable material to the outer surface of said first sheet at least partially overlies said side seams, and wherein the heat resistant material is disposed between the breathable material and a portion of said side seams such that the heat resistant material prevents the breathable material from being sealed to the outer surface of the front or back sheets.

The method may further comprise introducing an article into the pouch and sealing an opening of the pouch via a seam between the first and second sheets. In one embodiment, the method may also include the step of introducing a sterilization gas into an interior of the pouch through the breathable material.

Additional aspects of the invention are directed to a sterilizable container having a tray-like structure, such as a blister.

In one such embodiment, the container comprises a sheet of a flexible film that has been formed into a tray type-like structure so that the tray includes a bottom and a plurality of side walls defining an interior space of the tray for receiving an article to be sterilized. The tray also includes a continuous flange disposed on an upper portion of each of the plurality of walls. Preferably, the flanges extends about the periphery of the tray.

A breathable material is disposed overlying the interior space of the container and is joined to the flange with a continuous seam, such as heat seal between the breathable material and the surface of the flange. For example, in one embodiment, a continuous seam is located at or adjacent a peripheral edge of the breathable material joining the breathable material to a surface of the continuous flange. A heat resistant material is selectively disposed between the inner surface of the breathable material and the surface of the flange to selectively prevent the breathable material from sealing to the surface of the flange.

As noted above, the heat resistant material may comprise an adhesive material, such as a strip of tape.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide sterilizable containers that include a sheet material having a fibrous breathable material through which a sterilizing gas can be introduced into the interiors of the containers for sterilizing the contents of the container. The fibrous breathable material comprises a material through which a gas, such as a sterilizing gas can be introduced into the interior of the package.

As used herein, the term "container" is used in a generic sense, and should be recognized to include and packaging structure in which a sheet of fibrous breathable material is used in the packaging structure to provide a breathable membrane through which a sterilizing gas may be introduced into an interior of the container. Accordingly, the term container includes packages, pouches, sacks, bags, satchels, envelopes, packages having a rigid or semi-rigid support to which a breathable material is sealed to define a lidding or is part of the lidding of the container, and the like. Similarly, the term "pouch" is used in a generic sense and should be recognized to include, sacks, bags, satchels, packages, containers, and the like.

Figure 1:
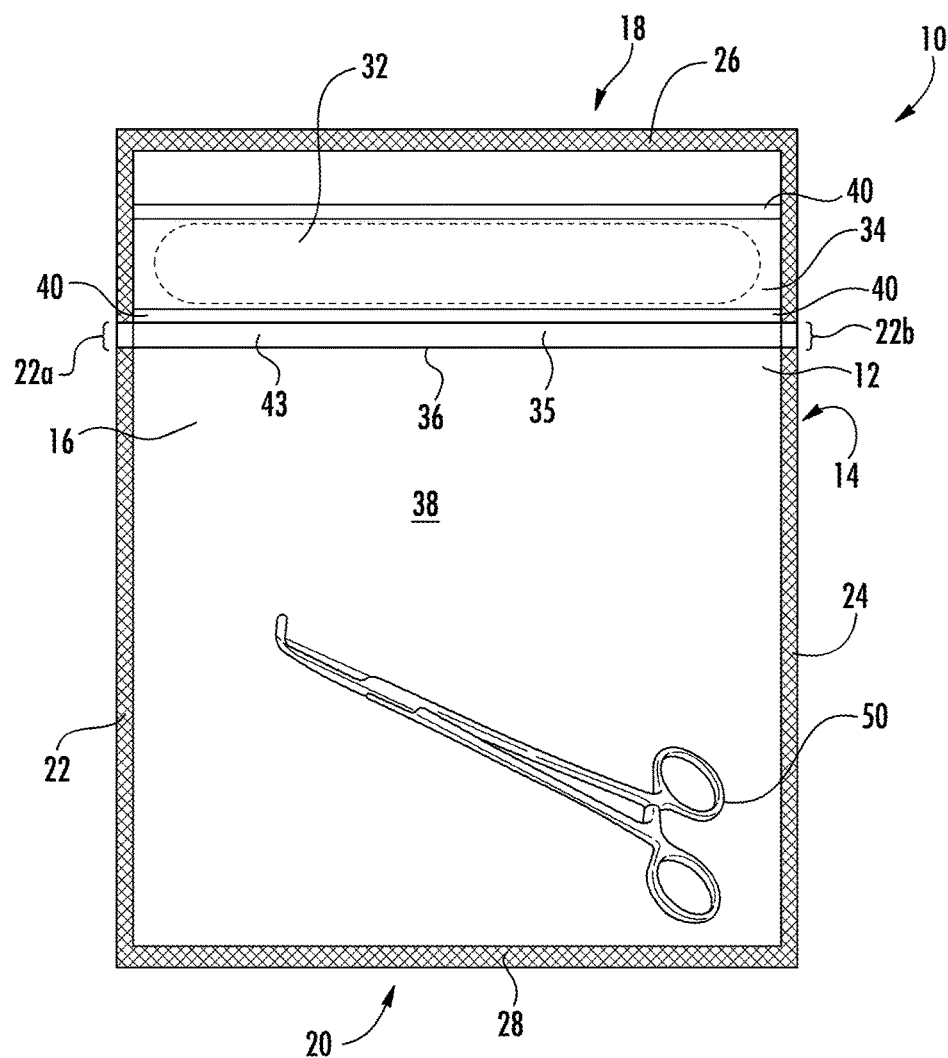
FIG. 1 is a plain view of a sterilizable pouch in accordance with one embodiment of the invention.
Figure 2:
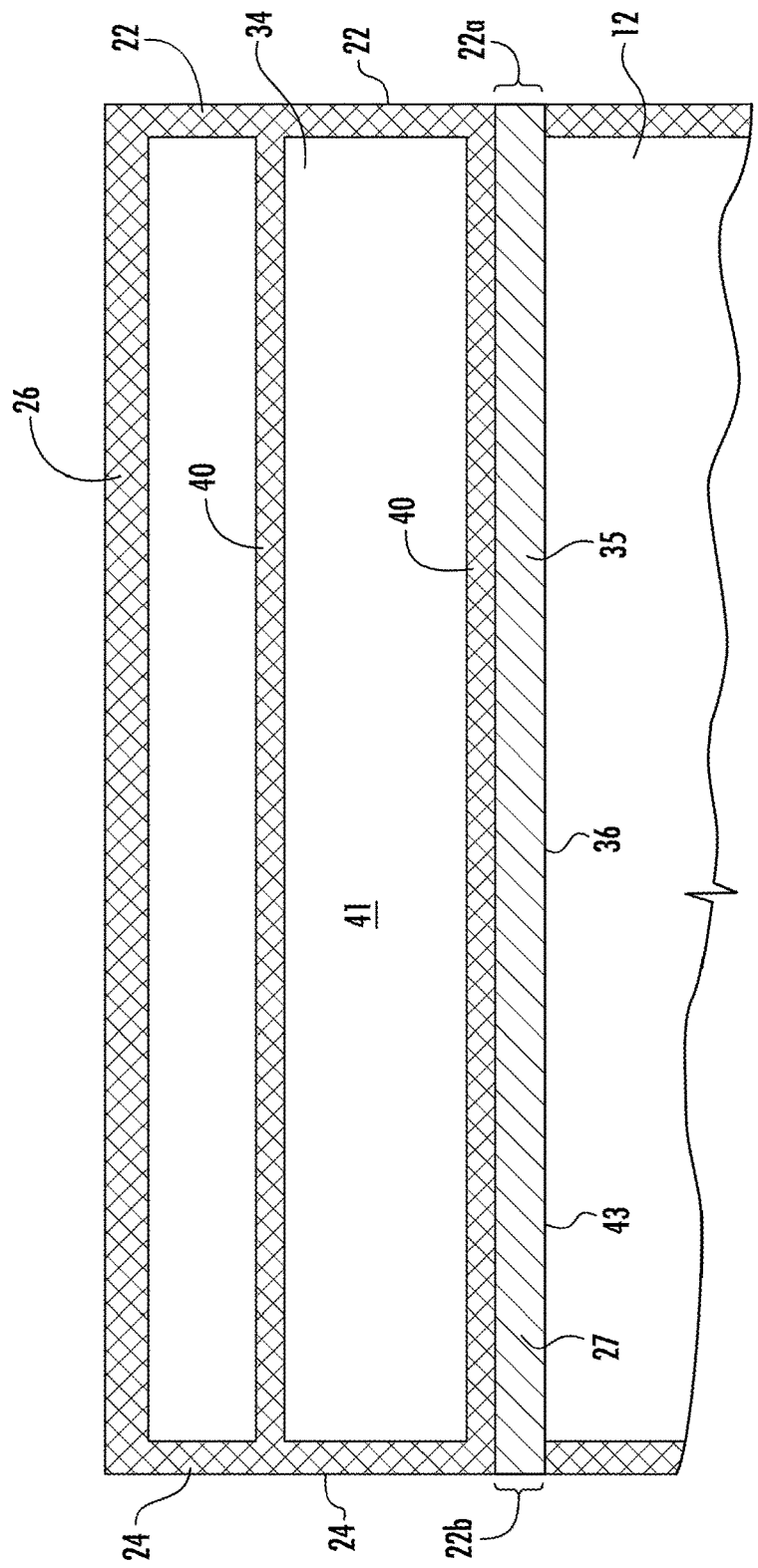
FIG. 2 is a plain view of an inner surface of the breathable material in which the remaining portions of the pouch are not shown.
Figure 3:
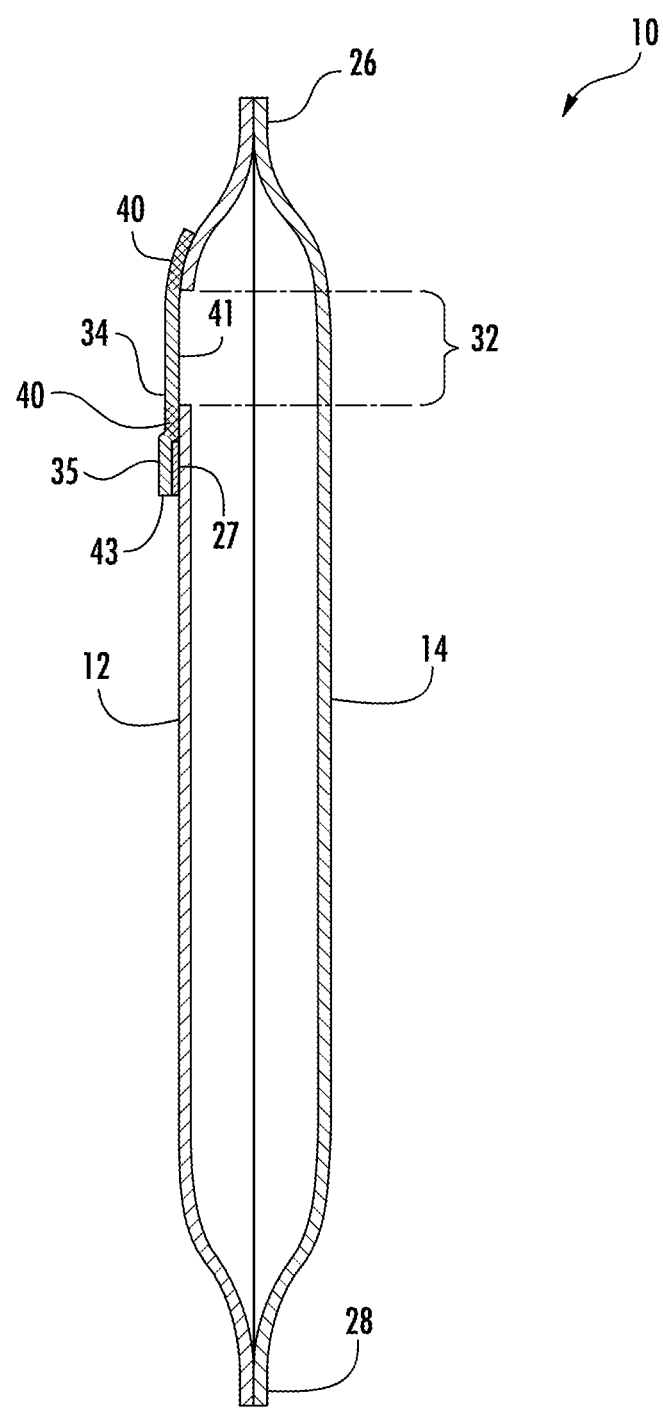
FIG. 3 is a cross section of the sterilizable pouch of FIG. 1.

Turning now to FIGS. 1-3, a sterilizable container in the form of a pouch is illustrated and designated by reference character 10. The pouch 10 comprises front and back sheets 12, 14 that are arranged in opposing face-to-face relation with each other and are interconnected to define an interior space 16 of the pouch. The pouch includes a top end 18, a bottom end 20, and a pair of opposing side seams 22, 24 that extend longitudinally between the top and bottom ends of the pouch. In the illustrated embodiments, the top end of the pouch is sealed with top seam 26 and the bottom end of the bag is sealed with bottom seam 28.

As described in greater detail below, the front and back sheets 12, 14 each individually comprise a flexible film comprised of a polymeric material having microbe barrier properties. In a preferred embodiment, the films comprising the front and back sheet each include liquid, moisture vapor, and gas barrier properties.

In the embodiment shown in FIGS. 1-3, the sterilizable pouch is shown in a sealed state with an article disposed in the interior space of the pouch. As discussed below, embodiments of the pouch can be prepared in which one of the ends of the pouch (e.g., the top or bottom end) is left open during manufacturing so as to provide an opening through which an article can be introduced into the pouch during the packaging process. The open end can then be sealed with a heat seal after an article has been inserted.

At least one of the front or back sheet includes an opening 32 formed therein and a breathable material 34 overlying and covering the opening. As discussed in greater detail below, the fibrous breathable material comprises a microbe barrier, gas permeable, material that permits a sterilizing gas to be introduced into the interior space of the pouch while preventing microorganisms from passing into the pouch. During sterilization, a sterilizing medium, such as a gas, is introduced through the breathable membrane and into the interior space of the pouch to sterilize an article 50 disposed therein.

In the illustrated embodiment, the opening 32 and the breathable material 34 are positioned towards a top portion of the front sheet 12. However, it should be recognized that the opening and breathable material can be positioned at other locations on the pouch including on the back sheet or towards a central or bottom portion of the front and back sheets. In addition, the pouch may include one or more such breathable openings as desired.

The breathable material 34 preferably comprises a sheet material that permits the passage of gases, including oxygen, carbon dioxide, and various sterilization gases, while limiting the passage of undesirable materials, such as microorganisms. Suitable materials for the breathable material may include nonwovens, medical grade paper, microbial barrier membranes, and other porous materials that limit the passage of microbes. Suitable nonwoven sheet materials include spunbond nonwoven fabrics, such as polypropylene and nonwoven fabrics formed of flash-spun polyethylene strands, such as a nonwoven sheet material sold by E.I. Du Pont de Nemours and Company under the trademark TYVEK®. In a preferred embodiment, the breathable material comprises an uncoated nonwoven fabric.

In one embodiment, the breathable material has a peripheral edge 36 and is joined to an outer surface 38 of front sheet 12 along a continuous seam 40 that is located towards or adjacent to the peripheral edge 36 of the breathable material 34. Preferably, the breathable material is joined to the sheet material with a heat seal.

In one embodiment of the sterilization pouch 10, the breathable material 34 includes an unsealed region 35 that is disposed along a portion of the peripheral edge 36 of the breathable material 34. The unsealed region 35 provides a lip that is unattached to the surface of the breathable material so as to provide a surface that can be grasped and pulled when peelably removing the breathable material from the pouch. For example, at a time when it is desirable to remove the contents of the pouch, an individual can open the pouch by grasping the unsealed region with his/her fingers and then apply a peeling force to peel back and remove the breathable material.

In the illustrated embodiment, the unsealed region 35 is disposed towards the bottom end 43 of the breathable material between the continuous seam 40 and the peripheral edge 36. However, it should be recognized that the unsealed region can be disposed at other locations along the peripheral edge 36 of the breathable material, such as, along the bottom or side ends of the breathable material. In one embodiment, the unsealed region 35 extends from about 0.5 to 15 cm beyond the continuous seam to the peripheral edge 36, and in particular, from about 0.5 to about 6 cm, and more particularly, from about cm 0.75 to about 1.25 cm.

As shown in the illustrated embodiments, a portion of the breathable material 34, overlies opposing side seams 22, 24 including a portion of the continuous seam 40, at the regions identified by reference characters 22a and 22b.

It has been found that when these regions 22a, 22b are part of the heat seal (continuous seam 40) forming side seams at 22, 24, fiber tear may occur at these regions when removing the breathable material to open the package. Generally, fiber structures, such as the fibrous breathable material are prone to fiber tear. When heat sealed together, the polymeric material comprising the outer surface of the front sheet flows around the edge of the fiber structure and becomes adhered to portions of fibers within the core or thickness of the breathable material. Generally, the bond between these fibers and the polymeric material is greater than the fiber-to fiber bond strength between individual fibers. As a result, fibers are more prone to tear when opening the package by pulling the breathable material away from the surface of the front sheet. Fiber tear typically generates undesirable loose particulates that can end up on sterile devices, and lead to a compromise of the sterile field.

To help prevent fiber tear, a heat resistant material is positioned between the fibrous breathable material and the outer surface 38 of front sheet 12 at regions 22a, 22b. The heat resistant material helps to prevent the melted polymeric material from contacting the breathable material at regions 22a, 22b, and thereby prevent bonding of the polymer to the fibers of the breathable material in these regions.

In this regard, FIGS. 2 and 3 show an embodiment of the pouch in which a heat resistant material 27 is positioned between the inner surface of the breathable material and an outer surface of the front sheet. More specifically, FIG. 2 shows a face (i.e., inner surface 41) of the breathable material that is normally sealed to the outer surface 38 of the front sheet 12. For purposes of illustration, the remaining portions of the front and back sheets of the pouch in FIG. 2 are not shown to allow the reader to see the features of the inner surface 41 of the breathable material. In other words, the inner surface 41 of breathable material is being viewed as if the reader is looking through the back sheet towards the front sheet. In the illustrated embodiment of FIGS. 2 and 3, the inner surface 41 includes a strip of heat resistant material 27 that is positioned between the inner surface 41 of the breathable material and the outer surface (see reference character 38 in FIG. 1) of the front sheet. As noted previously, the heat resistant material may extend continuously between opposing side seams (e.g., continuously between side seams 22 and 24), or may be discrete to regions 22a, 22b.

Preferably, the heat resistant material comprises an adhesive material (e.g., a tape) that extends along the unsealed region 35 of the breathable material, and is disposed towards the bottom end 43 of the breathable material between the continuous seam 40 and the peripheral edge 36.

The heat resistant material comprises a material that prevents the breathable material from sealing to the outer surface of the front sheet. In one embodiment, the heat resistant material comprises a film having a melting temperature that is greater than the temperature at which the heat seal is formed. For example, in one embodiment, the heat resistant material comprises a film having a melting point at least 10° C. higher than the melting temperature of the polymer forming the heat sealable surfaces of the front sheet (e.g., inner and outer surfaces of the front sheet), and more preferably, at least 10° C. higher, and even more preferably, at least 25° C. higher. In one embodiment, the melting point of the heat resistant material is 20° C. to 35° C. higher than the sealing temperature for sealing the breathable material to the outer surface of the front sheet. Examples of suitable film materials may include polyester and polypropylene.

The heat resistant material 27 may comprise distinct materials positioned at regions 22a, 22b, or alternatively, may extend continuously between opposing side seams 22, 24. In one embodiment, the heat resistant material 27 may comprises a film having an adhesive layer that adheres the heat resistant material 27 to the outer surface of the front sheet or an inner surface of the breathable material. Typically, the heat resistant material has a length and a width wherein the width of the heat resistant material may be from about 0.5 to 15 cm, and in particular, from about 0.5 to about 6 cm, and more particularly, from about cm 0.25 to about 1.25 cm. In a preferred embodiment, the width of the heat resistant material may be from about 0.5 to 1.0 cm.

In a preferred embodiment, the heat resistant material 27 comprises an adhesive tape that can be applied to the breathable material prior to sealing the breathable material to the outer surface of the front sheet. Alternatively, the breathable material may be applied to the outer surface of the front sheet. SCOTCH® tape is an example of a suitable heat resistant film that may be used in embodiments of the present invention.

Figure 4:
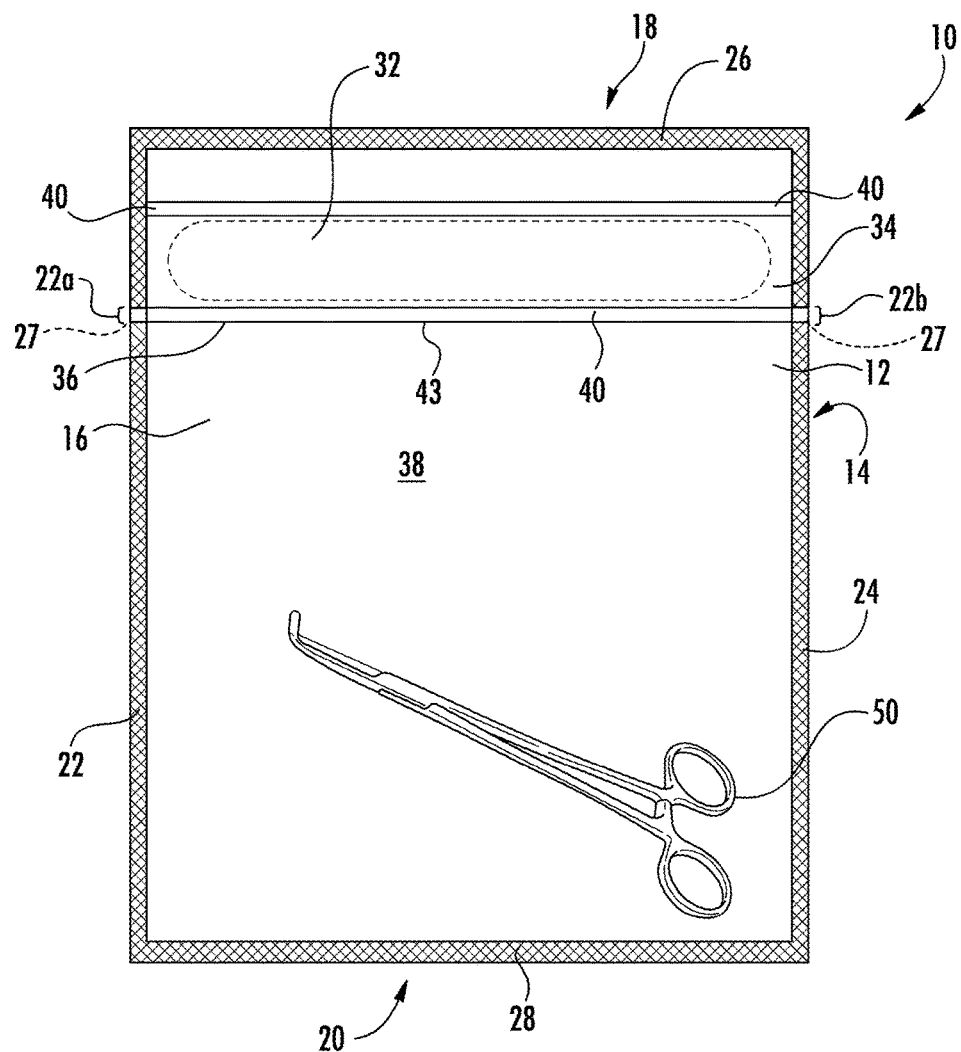
FIG. 4 is an alternative embodiment of the sterizilizable pouch.

With reference to FIG. 4, an embodiment of the pouch is shown wherein the heat resistant material is disposed at discrete regions (here, corresponding to regions 22a, 24a) between the inner face of the breathable material and the outer surface of the front sheet. In this embodiment, the heat resistant material prevents the breathable material from bonding to the outer surface at regions 22a, 22b.

The film in which the opening 32 is formed (the front sheet 12 in the illustrated embodiment) may comprise a single or a multilayer polymeric material, such as a multilayer film.

In one embodiment, the front film in which the opening is formed comprises a multilayer film having a peel feature such that the breathable material can be peelably removed from the outer surface of the front or back sheet without tearing of the breathable material. Examples of suitable films that may be used in aspects of the invention are described in copending U.S. Patent Application entitled Sterilization Pouch, application Ser. No. 13/677,475, Filed: Nov. 15, 2012, the contents of which are hereby incorporated by reference in their entirety.

The outer layer of the front sheet generally comprises a polymeric material that is heat sealable to the breathable material. Preferably, the outer layer is capable of forming a heat seal to the breathable material. The polymer forming the heat seal layer should be such that at the temperatures used to form heat seals, for example 110 to 180° C., it should have a sufficiently low viscosity that it penetrates into and around the fibers of the breathable material to which the film is being heat sealed. Penetration of the outer layer into the breathable material in general serves to effect a mechanical interlocking between the outer layer and the breathable material. The depth of penetration and the degree of interlocking generally depends upon the chemical composition and the relative quantities of the materials forming the outer layer, the fiber dimensions, packing and type, the openness of the sealing face of the breathable material, and the heat sealing temperature, pressure and dwell time.

In some embodiments, the front sheet includes an outer layer comprising a polymeric material having heat resistant properties. Suitable polymers for such an outer layer may include one or more of any of the following: polyolefins (e.g., polyethylenes, polypropylenes), polyamides, polyesters, and polystyrenes. Examples of suitable polyesters include amorphous (co)polyesters, poly(ethylene/terephthalic acid), and poly(ethylene/naphthalate). In a preferred embodiment, the front and back sheets include an outer layer 52 comprising polyethylene.

Polymeric films suitable for use as a film in pouches in accordance with the present invention may include one or more additional layers that impart desired properties to the film. For example, the film may include one or more functional layers, bulk layers, tie layers, and the like. For example, the film may include one or more interior core layers. In one embodiment, the interior core layer may be composed of compositions selected to impart specific properties to the film, such as barrier properties. Suitable components the film may include metallic foil, such as aluminum foil, and metallized films, such aluminized films, aluminum oxide films (AlOx), silicon oxide films (SiOx), and films comprising polychlorotrifluoroethylene (PCTFE) such as ACLAR®. The film may also include polymeric components having barrier properties, such as ethylene/vinyl alcohol copolymer ("EVOH"), vinylidene chloride polymers ("PVdC"), polyalkylene carbonate, polyester (e.g., PET, PEN), polyacrylonitrile ("PAN"), and polyamides.

Useful polyamides may include polyamide 6, polyamide 9, polyamide 10, polyamide 11, polyamide 12, polyamide 66, polyamide 610, polyamide 612, polyamide 61, polyamide 6T, polyamide 69, copolymers made from any of the monomers used to make two or more of the foregoing homopolymers (e.g., copolyamide 6/12, polyamide 12, copolyamide 66/69/61, copolyamide 66/610, copolyamide 6/66, and copolyamide 6/69), and blends of any of the foregoing homo- and/or copolymers.

The film may also include a sealant layer on the opposite side of the film from the heat sealable outer layer. The sealant layer typically defines an inner surface of the sterilizable pouch that faces the interior space of the pouch. The polymer material (i.e., component or blend of components) that forms the sealant layer has a melting point that facilitates heat sealing the inner surface of the sheet material to a second sheet material, such as in the embodiment illustrated in FIG. 1, or to itself. Useful material for this sealant layer may include the ones mentioned above in connection with the outer layer.

Sterilizable pouches in accordance with the present invention can be used to package a variety of different articles including medical instruments and devices. For example, the sterilizable pouch can be used to package and sterilize, scalpels, scissors, sutures, forceps, retractors, blades, clamps, stents, both treated and untreated, catheters, surgical drapes and gowns, surgical and procedural kits, etc.

Sterilizable pouches in accordance with the present invention can be prepared using methods commonly used in forming pouches/bags. For example, in one embodiment pouches in accordance with the present invention can be prepared by separately providing two distinct film sheets of material that are to define the front and back sheets. Generally, the film sheets are provided via a roll stock material from which each sheet material is unwound. At least one of the sheet materials includes a cut-out or hole which will form the opening of the breathable material (see reference number 32 in FIG. 1). The opening can be formed in the film prior to being wound onto the roll stock or, alternatively, can be formed in the sheet material just prior to forming the pouch. The opening 32 can be made in the film comprising the front or back sheets in a variety ways as known in the art, including punching, die cutting, cutting, and the like.

Referring back to FIG. 1, the breathable membrane in the front or back sheet can be formed by heat sealing the breathable material to the outer surface of the film to form continuous seam 40. Preferably, the heat resistant material 27 is attached to the inner surface of the breathable material, or the outer surface of the front sheet prior to joining the breathable material to the outer surface of the film. As in the formation of the opening in the film, the breathable material can sealed to the film prior to being wound onto the roll stock or, alternatively, can be attached to the film just prior to forming the pouch. That is, prior to forming one or more of the opposing side seams that collectively define the interior of the pouch.

In one embodiment the films defining the front and back sheets 12, 14 are superimposed opposite to each other and are then joined to each other along the opposed side seams 22, 24. The side seams, as well as the other seams of the pouch to be described presently, can be formed by any of various methods conventionally used in the packaging industry provided the seams are substantially impervious to the ingress/egress of liquids and gases. Preferably, the various seams are substantially impervious to gases such as moisture vapor, oxygen, carbon dioxide, etc. Suitable methods for forming the seams may include adhesive or fusion bonding, such as by forming seals with heat or ultrasonic energy. In the particular embodiment illustrated, the front and back sheets are made from a heat sealable material and the various seams are formed by producing a fusion bond or seal between contacting interior surfaces of the front and back sheets using pressure and heat or ultrasonic energy as is well known. Although referred to herein as "heat seals", it should be understood that this term is intended to apply both to seals formed by heating the contacting surfaces with a heated anvil or platen, as well as to heating and fusion produced by other methods, such as application of ultrasonic energy.

During manufacturing of the pouch, one of the ends of the pouch (e.g., the top end 18 or the bottom end 20) is typically open so that an opening is provided for introducing an article into the interior space of the pouch. Once an article is introduced into the pouch, a heat seal can be used to bond the inner surfaces of the front and back sheets to each other and thereby form top seam 26 or bottom seam 28.

Alternatively, a pouch can be prepared from a single sheet of film in which the film is center folded to form a c-fold in the film, which in turn defines the front and back sheets disposed opposite each other.

Figure 5:
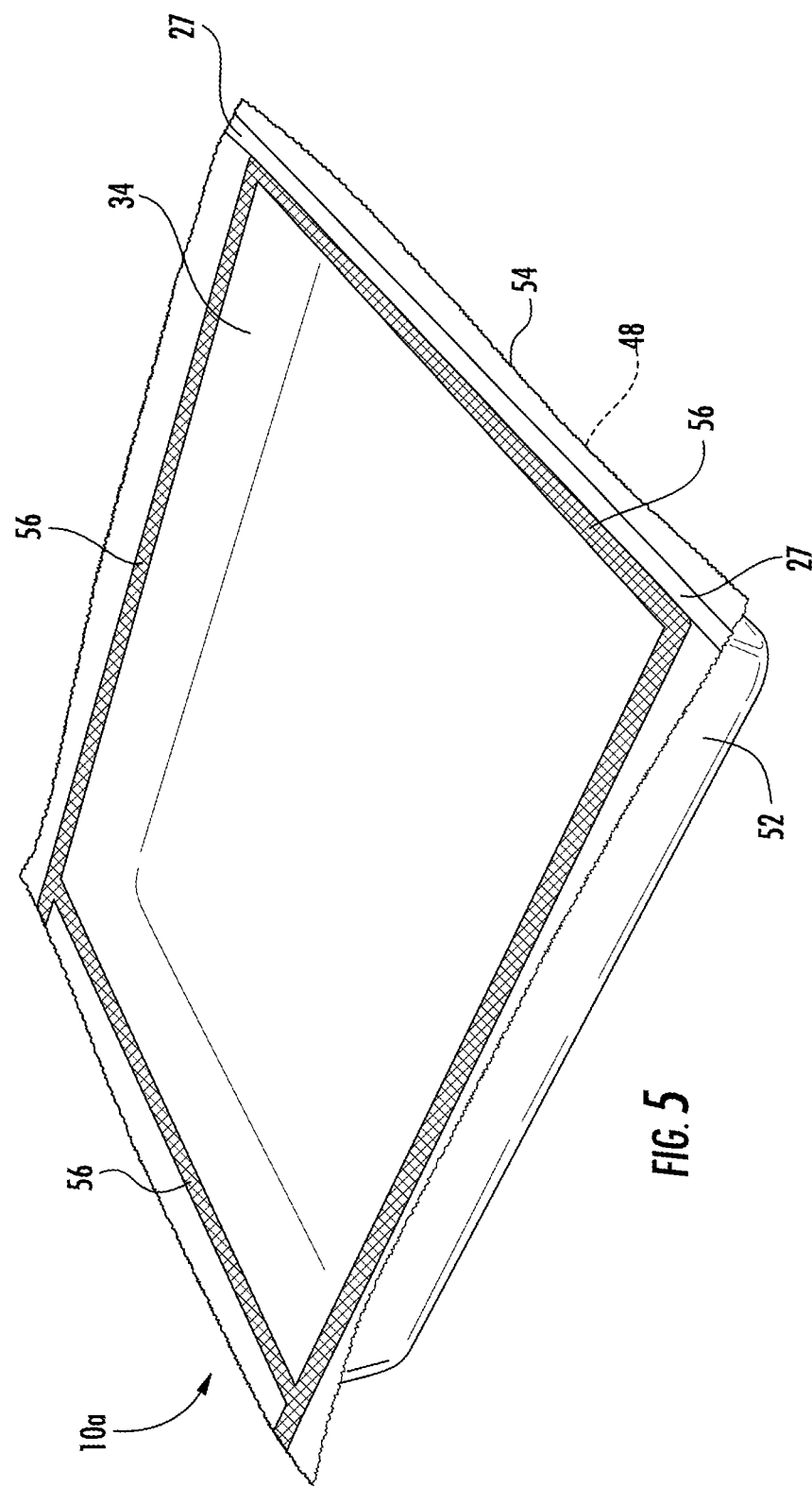
FIG. 5 is a perspective view of an alternative embodiment of the invention.

In another aspect, embodiments of the present invention a container comprising a support member to which a film of breathable material is affixed via a heat seal. In this regard, FIG. 5 illustrates a variation of a sterilizable package 10*a* comprising a support member 52 (e.g., tray) to which a sheet of breathable material 34 has been adhered to form a lidding 54. In this embodiment, breathable material 34 is adhered to flange 48 to sealably close the package. Flange 48 defines a lip of the support member to which the lidding may be sealably attached via a heat seal.

Preferably, sheet material is affixed to the support member 52 with a heat seal. The sterilizable package includes heat seal 56 joining the breathable material and support member to each other. Heat seal 56 extends around the periphery of the sheet material where the sheet material is affixed to the support member.

Preferably, a strip of heat resistant material 27 is positioned between the breathable material and the support member along at least one edge of the breathable material. As in the embodiment of the pouch discussed previously, the heat resistant material prevents the molten polymeric material of the support member from sealing to the breathable material. Preferably, a portion of the breathable material overlying a portion of a flange of the support member is not attached to the flange, and thereby provides a portion of the breathable material that can be grasped for removing the breathable material from the support member. As a result, fiber tear during removable of the breathable material may be minimized.

In embodiments in which the support member is thermoformed, the support member may be thermoformed in-line with the packaging operation or provided preformed. Depending on the product being packaged and the ultimate end-use application the support member may be gas permeable or substantially gas impermeable. Additionally, depending on the composition of the inner surface of the sheet material (i.e., the surface affixed to the support member) the support member may comprise a heat sealable material. For example, the support member may include a sealant film for heat sealing the support member to breathable material 34.

In a preferred embodiment, the support member 52 comprises a thermoplastic material has been thermoformed into a tray as is known in the art.

Seal 56 can be made peelable so that the lidding 54 can be easily removed during use. In peelable applications, the peal strength of seal 56 is typically about 0.5 to 4 pounds per inch. In contrast to prior art packaging applications in which the lidding or a sheet of the pouch comprises a sheet of the breathable material, such as Tyvek®, the present invention makes it possible to use less breathable material, in the lidding or the pouch while still being able to maintain the same sterilizable properties, and also makes it possible to prepare peelable applications that do not need a coating on the breathable material, such as a coated Tyvek®.

Figure 6:
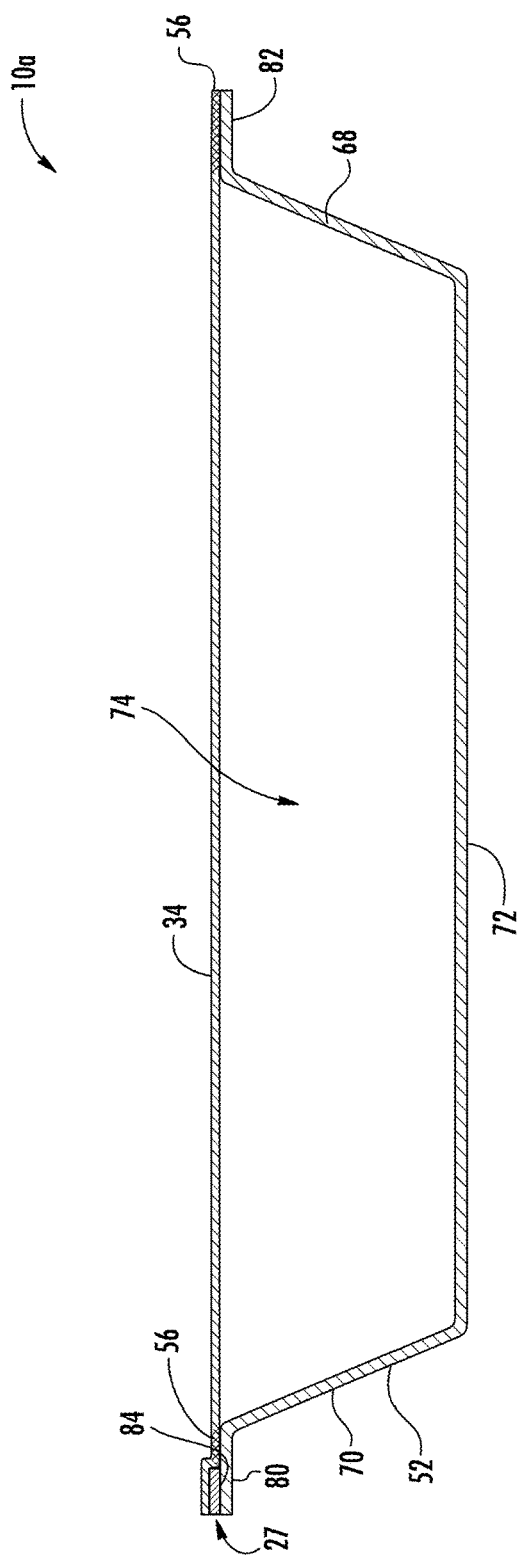
FIG. 6 is a cross-section of the embodiment of FIG. 5.

FIG. 6 is a cross-section of the container of FIG. 5. As shown, the support member includes sidewalls 68, 70, and bottom wall 72 defining tray 52 having an interior space 74 for receiving an article therein. Preferably, sidewalls of the tray are continuous.

The sidewalls of the tray include upper portion 80 defining a flange 82 having an upper surface 84 to which the breathable material 34 may be attached via a heat seal. A heat resistant material 27 is disposed along at least one edge of the flange between the upper surface 84 and the breathable material to prevent the breathable material from being sealed to the support member. Preferably, the unsealed portion of the breathable material defined by presence of the breathable material provides an unsealed edge that helps prevent and minimize fiber tear as well as creating a peel tab that may be used by the end user in opening the container.

Additional embodiments of the invention are described in U.S. patent application Ser. No. 13/677,475, the contents of which are hereby incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A sterilizable pouch comprising:
   front and back sheets of a flexible polymeric film joined to each other along opposing side and bottom edges to define a pouch having an interior space for receiving an article therein;
   an opening formed in at least one of the front or back sheets, the opening for providing communication between an exterior environment of the pouch and said interior space;
   a breathable material overlying and covering said opening, and being joined to an outer surface of said front or back sheet with a continuous heat seal, said breathable material comprising a fibrous a nonwoven or medical grade paper material that is impervious to microorganisms, but pervious to gases,
   a heat resistant material selectively disposed between the breathable material and the outer surface of the front or back sheet to prevent the breathable material from sealing to the outer surface of the front or back sheet, wherein the heat resistant material comprises a polymer material having a melting temperature higher than that of the film to which the breathable material is attached, and wherein the heat resistant material is disposed between a peripheral edge of breathable material and the continuous heat seal.

2. The pouch of claim 1, wherein the heat resistant material comprises a strip of adhesive tape attached to an inner surface of the breathable material.

3. The pouch of claim 1, wherein the heat resistant material is disposed between the breathable material and at least a portion of the side edges of the pouch.

4. The pouch of claim 1, wherein the continuous heat seal joining the breathable material includes a lower portion that is disposed below the opening such that said lower portion is disposed towards the bottom edge of the pouch, and wherein the heat resistant material is disposed between said lower portion and a peripheral edge of the breathable material.

5. The pouch of claim 4, wherein the heat resistant material extends between opposing side edges of the pouch.

6. The pouch according to claim 1, wherein the breathable material includes a lip that is unconnected to the film and that extends between the continuous seam and a peripheral edge of the breathable material.

7. The pouch according to claim 6, wherein said lip extends between the continuous seam and a peripheral edge from about 0.5 to about 15 cm, and wherein the heat resistant material is attached to an inner surface of the breathable material along said lip.

8. The pouch of claim 1, wherein the breathable material comprises an uncoated spunbond nonwoven fabric.

9. The pouch according to claim 1, wherein the opposing side edges of the front and back sheets are joined to each other with a heat seal defining side seams of the pouch, and wherein the continuous heat seal joining the breathable material to the outer surface of said front sheet at least partially overlies said side seams, and wherein the heat resistant material is disposed between the breathable material and a portion of said side seams such that the heat resistant material prevents the breathable material from being sealed to the outer surface of the front or back sheets.

10. The pouch according to claim 1, wherein front and back sheets each include opposing top edges that are unconnected to each other to define an access opening into the interior space of the pouch.

11. A sterilizable pouch comprising:
front and back sheets of a flexible polymeric film arranged in opposing face-to-face relation, each having an inner surface comprising a heat sealable thermoplastic material on opposite surfaces, a top edge, a bottom edge, and opposite side edges extending longitudinally from said top edge to said bottom edge;
side seams extending longitudinally along said opposite side edges and joining the front and back sheets to each other;
a bottom seam extending transversely along said bottom edges and joining the front and back sheets to each other;
an opening formed in the front sheet and providing communication between an exterior environment of the pouch and an interior space of the pouch;
a breathable material disposed on the front sheet and covering said opening, said breathable material comprising a nonwoven or medical grade paper material that is moisture vapor permeable and water-impermeable; and
a continuous seam located at or adjacent the peripheral edge of the breathable material joining the breathable material to the outer layer of the front sheet,
a heat resistant material disposed on an inner surface of the breathable material between the front sheet and the breathable material, wherein presence of the heat resistant material defines a region in which the breathable material is not joined to the front sheet, wherein the heat resistant material comprises a polymer material having a melting temperature higher than that of the film to which the breathable material is attached, and wherein the heat resistant material is disposed between a peripheral edge of breathable material and the continuous heat seal.

12. The pouch of claim 11, wherein the breathable material is a nonwoven fabric formed flash-spun polyethylene strands.

13. The pouch of claim 11, wherein the breathable material comprises a nonwoven fabric.

14. The pouch of claim 11, wherein the top edges of the front and back sheet are unconnected to each other to define an access opening into the interior space of the pouch.

15. The pouch of claim 11, wherein the heat resistant material extends between opposing side edges of the pouch.

16. The pouch of claim 11, wherein the heat resistant material does not extend between opposing side edges of the pouch, and is positioned in discrete locations between the side seams and the breathable material.

17. The pouch of claim 11, wherein the heat resistant material comprises an adhesive strip having a film layer and an adhesive layer, wherein the adhesive layer joins the film layer to an inner surface of the breathable material.

18. The pouch of claim 11, wherein the heat resistant material has a melting temperature that is higher than the melting temperature of a polymer forming a heat sealable surface of the front and back sheets.

19. The pouch of claim 18, wherein the melting point of the heat resistant material is higher than a sealing temperature for sealing the breathable material to an outer surface of the front sheet.

20. A method of making a sterilizable pouch comprising the steps of
forming an opening in a first sheet material of a flexible polymeric film;
providing a breathable material having a heat resistant material joined to a surface of the breathable material, breathable material comprising a fibrous nonwoven or medical grade paper, and the heat resistant material comprising a polymer material having a melting temperature higher than that of the film to which the breathable material is attached;
affixing the breathable material to an outer surface of the first sheet material with a continuous heat seal such that the breathable material overlies and covers said opening, wherein the heat resistant material is disposed between the outer surface of the first sheet and the breathable material; and
joining a second sheet material of a flexible polymeric film to an opposite surface of the first sheet material via a plurality of side seams and a bottom seam to form a pouch having an interior space, wherein the heat resistant material prevents the inner surface of the breathable material from sealing to the outer surface of the front sheet.

21. The method of claim 20, wherein first and second sheets each include opposing top edges that are unconnected to each other to define an access opening into an interior space of the pouch.

22. The method of claim 20, wherein the breathable material is affixed to the first sheet prior to joining the first and second sheets to each other.

23. The method of claim 20, wherein the breathable material is affixed to the first sheet after joining the first and second sheets to each other.

24. The method of claim 20, wherein the opposite side edges of the first and second sheets are joined to each other with a heat seal defining side seams of the pouch, and wherein the continuous heat seal joining the breathable material to the outer surface of said first sheet at least partially overlies said side seams, and wherein the heat resistant material is disposed between the breathable material and a portion of said side seams such that the heat resistant material prevents the breathable material from being sealed to the outer surface of the front or back sheets.

25. The method of claim 20, further comprising introducing an article into the pouch and sealing an opening of the pouch via a seam between the first and second sheets.

26. The method of claim 25, further comprising the step of introducing a sterilization gas into an interior of the pouch through said breathable material.

27. A sterilizable container comprising:
- a sheet of a flexible film formed into a tray type-like structure, the tray having bottom and a plurality of side walls defining an interior space for receiving an article to be sterilized;
- a continuous flange disposed on an upper portion of each of the plurality of walls, and extending about the periphery of the tray;
- a breathable material disposed overlying the interior space of the container, said breathable material comprising a fibrous uncoated nonwoven or medical grade paper material that is moisture vapor permeable and water-impermeable; and
- a continuous seam located at or adjacent a peripheral edge of the breathable material joining the breathable material to a surface of the continuous flange; and,
- a heat resistant material selectively disposed between the inner surface of the breathable material and the surface of the flange to selectively prevent the breathable material from sealing to the surface of the flange, wherein the heat resistant material comprises a polymer material having a melting temperature higher than that of the sheet of flexible film to which the breathable material is attached, and wherein the heat resistant material is disposed between a peripheral edge of breathable material and the continuous heat seal.

* * * * *